United States Patent
Kapadia (10) Patent No.: US 11,478,311 B2
(45) Date of Patent: Oct. 25, 2022

(54) INTERFACES FOR SURGICAL SYSTEMS

(71) Applicant: Covidien LP, Mansfield, MA (US)

(72) Inventor: Jaimeen Kapadia, Cambridge, MA (US)

(73) Assignee: Covidien LP, Mansfield, MA (US)

(*) Notice: Subject to any disclaimer, the term of this patent is extended or adjusted under 35 U.S.C. 154(b) by 703 days.

(21) Appl. No.: 16/502,280

(22) Filed: Jul. 3, 2019

(65) Prior Publication Data
US 2019/0321114 A1    Oct. 24, 2019

Related U.S. Application Data (62) Division of application No. 15/114,892, filed as application No. PCT/US2014/064472 on Nov. 7, 2014, now Pat. No. 10,363,104.
(Continued)

(51) Int. Cl.
*A61B 34/30* (2016.01)
*A61B 34/35* (2016.01)
(Continued)

(52) U.S. Cl.
CPC ........ *A61B 34/30* (2016.02); *A61B 17/00234* (2013.01); *A61B 34/35* (2016.02);
(Continued)

(58) Field of Classification Search
CPC .............. A61B 34/35; A61B 17/00234; A61B 2018/00172; A61B 2018/00208;
(Continued)

(56) References Cited

U.S. PATENT DOCUMENTS 2,602,308 A   7/1952  Bonnet
3,583,139 A   6/1971  Purrer
(Continued)

FOREIGN PATENT DOCUMENTS

CN   102014759 A    4/2011
WO   2009151205 A1  12/2009
(Continued)

OTHER PUBLICATIONS

European Search Report dated Aug. 24, 2017, corresponding to European Application No. 14881189.6; 13 pages.
(Continued)

*Primary Examiner* — Nathaniel C Chukwurah (57) ABSTRACT

An interface for a surgical system includes an instrument drive unit and a surgical instrument. The instrument drive unit includes a connection hub and at least one drive shaft rotatably supported in the connection hub. The at least one drive shaft extends between a first end and a second end having an oblique end surface. The surgical instrument is releasably connectable to the instrument drive unit and includes a connecting member and at least one driven shaft rotatably supported in the connecting member. The at least one driven shaft extends between a first end and a second end. The second end has an oblique end surface corresponding to the oblique end surface of the at least one drive shaft. The oblique end surfaces are configured such that the connecting member is connectible with the connection hub via a first connection pathway and a second connection pathway.

20 Claims, 11 Drawing Sheets

Related U.S. Application Data (60) Provisional application No. 61/934,228, filed on Jan. 31, 2014.

(51) Int. Cl.
  *F16D 1/02* (2006.01)
  *B25J 15/04* (2006.01)
  *F16D 1/10* (2006.01)
  *A61B 17/00* (2006.01)
  *A61B 18/00* (2006.01)

(52) U.S. Cl.
  CPC ............ *B25J 15/0408* (2013.01); *F16D 1/02* (2013.01); *F16D 1/101* (2013.01); *A61B 2017/0053* (2013.01); *A61B 2017/00477* (2013.01); *A61B 2018/00172* (2013.01); *A61B 2018/00208* (2013.01); *F16D 2001/102* (2013.01)

(58) Field of Classification Search
  CPC ...... F16D 1/10; F16D 1/101; F16D 2001/102; F16B 5/0628; B25J 15/04; B25J 15/0408; B25J 15/0425
  See application file for complete search history.

(56) References Cited

U.S. PATENT DOCUMENTS

| | | | |
|---|---|---|---|
| 4,897,014 A | 1/1990 | Tietze | |
| 5,921,992 A | 7/1999 | Costales et al. | |
| 6,306,126 B1 | 10/2001 | Moctezuma | |
| 6,331,181 B1 | 12/2001 | Tierney et al. | |
| 6,416,415 B1 | 7/2002 | Yu | |
| 6,824,471 B2 | 11/2004 | Kamenov | |
| 6,994,708 B2 | 2/2006 | Manzo | |
| 6,996,487 B2 | 2/2006 | Jutras et al. | |
| 7,524,320 B2 | 4/2009 | Tierney et al. | |
| 7,809,184 B2 | 10/2010 | Neubauer et al. | |
| 7,947,051 B2 | 5/2011 | Lee et al. | |
| 7,963,913 B2 | 6/2011 | Devengenzo et al. | |
| 8,021,326 B2 | 9/2011 | Moll et al. | |
| 8,183,520 B2 | 5/2012 | Prisco | |
| 8,394,054 B2 | 3/2013 | Wallace et al. | |
| 8,479,969 B2 | 7/2013 | Shelton, IV | |
| 8,992,113 B2 | 3/2015 | Campagna et al. | |
| 10,363,104 B2 | 7/2019 | Kapadia | |
| 2001/0008343 A1 | 7/2001 | Herdin et al. | |
| 2004/0054489 A1 | 3/2004 | Moctezuma De La Barrera et al. | |
| 2004/0143243 A1 | 7/2004 | Wahrburg | |
| 2004/0254680 A1 | 12/2004 | Sunaoshi | |
| 2006/0264742 A1 | 11/2006 | Neubauer et al. | |
| 2008/0058861 A1 | 3/2008 | Cooper et al. | |
| 2008/0065105 A1 | 3/2008 | Larkin et al. | |
| 2008/0103491 A1 | 5/2008 | Omori et al. | |
| 2008/0228195 A1 | 9/2008 | von Jako et al. | |
| 2008/0262513 A1 | 10/2008 | Stahler et al. | |
| 2009/0036902 A1 | 2/2009 | DiMaio et al. | |
| 2009/0044655 A1 | 2/2009 | DeLouis et al. | |
| 2009/0163930 A1 | 6/2009 | Aoude et al. | |
| 2009/0171197 A1 | 7/2009 | Burger et al. | |
| 2009/0326324 A1 | 12/2009 | Munoz Martinez et al. | |
| 2010/0082041 A1 | 4/2010 | Prisco | |
| 2010/0318101 A1 | 12/2010 | Choi | |
| 2010/0332031 A1 | 12/2010 | Itkowitz et al. | |
| 2011/0015650 A1* | 1/2011 | Choi ..................... A61B 34/30 606/130 |
| 2011/0015850 A1 | 1/2011 | Tange et al. | |
| 2011/0224825 A1 | 9/2011 | Larkin et al. | |
| 2012/0116416 A1 | 5/2012 | Neff et al. | |
| 2012/0289973 A1 | 11/2012 | Prisco et al. | |
| 2013/0218024 A1 | 8/2013 | Boctor et al. | |
| 2014/0001234 A1 | 1/2014 | Shelton, IV et al. | |
| 2016/0294092 A1 | 10/2016 | Kikuchi et al. | |

FOREIGN PATENT DOCUMENTS

| | | |
|---|---|---|
| WO | 2010126127 A1 | 11/2010 |
| WO | 2013159933 A1 | 10/2013 |

OTHER PUBLICATIONS

International Search Report for (PCT/US2014/064472) date of completion is Feb. 13, 2015 (6 pages).

Chinese Office Action (with English translation), dated Jul. 20, 2018, corresponding to Chinese Application No. 201480073374.4; 29 total pages.

European Office Action dated Aug. 7, 2018, corresponding to European Application No. 14 881 189.6; 8 pages.

Chinese Office Action dated Aug. 17, 2022, issued in corresponding CN Application No. 202010009813, 13 pages.

* cited by examiner

INTERFACES FOR SURGICAL SYSTEMS

CROSS-REFERENCE TO RELATED APPLICATIONS

This application is a Divisional Application of U.S. patent application Ser. No. 15/114,892, filed on Jul. 28, 2016, which is a U.S. National Stage Application filed under 35 U.S.C. § 371(a) of International Patent Application Serial No. PCT/US2014/064472, filed Nov. 7, 2014, which claims the benefit of U.S. Provisional Patent Application Ser. No. 61/934,228, filed Jan. 31, 2014, the entire disclosure of each of which is incorporated by reference herein.

BACKGROUND

Robotic surgical systems, such as, for example, a da Vinci® Surgical system have been used in minimally invasive medical procedures. Some robotic surgical systems include a console supporting a robot arm and a surgical instrument or at least one end effector that includes forceps or a grasping tool that is mounted to the robot arm. The robot arm provides mechanical power to the surgical instrument for its operation and movement. Each robot arm may include an instrument drive unit having a mechanical interface that is operatively connected to a corresponding mechanical interface of the surgical instrument.

Prior to or during use of the robotic system, surgical instruments are selected and connected to the instrument drive units of each robot arm. For proper installation to be completed, certain connecting features of the surgical instrument must be matingly engaged to corresponding connecting features of the instrument drive unit. Once these features are matingly engaged, the instrument drive unit can drive the actuation of the surgical attachment. However, the position and orientation of the connecting features of the surgical instrument relative to the connecting features of the instrument drive unit are often unknown, which makes aligning the connecting features with one another difficult.

Accordingly, before the surgical instrument can be considered properly connected to the instrument drive unit, the surgical system must calibrate the position of the connecting features of the surgical instrument relative to the position of the connecting features of the instrument drive unit. This is sometimes accomplished by rotating the connecting features of the instrument drive unit back and forth until the connecting features of the instrument drive unit find the corresponding connecting features of the surgical instrument. This trial and error approach to installing the surgical instrument with the instrument drive unit can be difficult, time consuming and problematic.

Therefore, there is a need for a more precise and efficient approach to connecting an instrument drive unit and a surgical instrument that, inter alia, obviates the need for calibration.

SUMMARY

In accordance with an aspect of the present disclosure, an interface for a surgical system is provided. The interface includes an instrument drive unit including a connection hub and at least one drive shaft rotatably supported in the connection hub. The at least one drive shaft extends between and has a first end configured for connection with a motor and a second end having an oblique end surface. The interface further includes a surgical instrument releasably connectable to the instrument drive unit. The surgical instrument includes a connecting member and at least one driven shaft rotatably supported in the connecting member. The at least one driven shaft extends between and has a first end and a second end. The second end has an oblique end surface corresponding to the oblique end surface of the at least one drive shaft of the instrument drive unit. The oblique end surfaces are configured such that the connecting member of the surgical instrument is connectible with the connection hub of the instrument drive unit via a first connection pathway and a second connection pathway. The second connection pathway is oriented transversely relative to the first connection pathway.

In some embodiments, when the connecting member of the surgical instrument is connected to the connection hub of the instrument drive unit, the oblique end surfaces may be engaged with one another and relative rotation therebetween is resisted.

In an aspect of the present disclosure, the oblique end surfaces may be configured such that upon engagement of the second end of the at least one drive shaft of the instrument drive unit with the second end of the at least one driven shaft of the surgical instrument, the at least one driven shaft of the surgical instrument may rotate to orient the oblique end surface of the at least one driven shaft of the surgical instrument into flush engagement with the oblique end surface of the at least one drive shaft of the instrument drive unit. It is contemplated that each oblique end surface may define a plane such that when corresponding oblique end surfaces are engaged, the planes of the corresponding oblique end surfaces are parallel to one another. The oblique end surfaces may have an ovate configuration.

In some embodiments, the oblique end surface of one of the at least one drive shaft and the at least one driven shaft may be concave and another of the at least one drive shaft and the at least one driven shaft may be convex.

In another aspect of the present disclosure, the connection hub may include a pair of spaced apart opposed sidewalls extending therefrom. The pair of sidewalls may include an axially translatable protrusion. The connecting member may include a cavity defined therein configured for receipt of the axially translatable protrusion to detachably secure the connection hub and the connecting member.

In embodiments, the at least one drive shaft of the instrument drive unit can include a plurality of drive shafts rotatably supported in the connection hub in a straight-lined configuration. The at least one drive shaft of the instrument drive unit may include a plurality of drive shafts rotatably supported in the connection hub in a staggered configuration.

In some embodiments, the second end of the at least one drive shaft of the instrument drive unit may include a radial extension disposed adjacent the oblique end surface thereof.

In accordance with another aspect of the present disclosure, an interface for a surgical system is provided. The interface includes an instrument drive unit and a surgical instrument. The instrument drive unit includes a connection hub and a plurality of drive shafts rotatably supported in the connection hub. Each of the plurality of drive shafts extend between and have a first end configured for connection with a motor and a second end extending perpendicular from the connection hub. The second end has a planar, oblique end surface.

The surgical instrument includes a plate and a plurality of driven shafts rotatably supported in the plate. Each of the plurality of driven shafts extends between and has a first end and a second end extending perpendicular from the plate. The second end has a planar, oblique end surface corresponding to a respective one of the oblique end surfaces of the plurality of drive shafts of the instrument drive unit. The oblique end surfaces are configured such that the plate of the surgical instrument is connectible with the connection hub of the instrument drive unit via a first connection pathway and a second connection pathway. The second connection pathway is oriented transversely relative to the first connection pathway.

In embodiments, each oblique end surface may define a plane such that when corresponding oblique end surfaces are engaged, the planes of the corresponding oblique end surfaces are parallel to one another. It is envisioned that the oblique end surfaces may be configured such that upon engagement of the second ends of the plurality of drive shafts of the instrument drive unit with the second ends of the plurality of driven shafts of the surgical instrument, the plurality of driven shafts may rotate to orient the oblique end surfaces of the plurality of driven shafts into flush engagement with corresponding oblique end surfaces of the plurality of drive shafts.

In some embodiments, the plurality of drive shafts of the instrument drive unit may be rotatably supported in the connection hub in a staggered configuration.

In accordance with a further aspect of the present disclosure, a method of assembling a surgical system is provided. The method comprises providing an instrument drive unit. The instrument drive unit includes a connection hub and at least one drive shaft rotatably supported in the connection hub. The at least one drive shaft extends between and has a first end configured for connection with a motor and a second end. The second end has an oblique end surface.

The method further includes providing a surgical instrument. The surgical instrument includes a connecting member and at least one driven shaft rotatably supported in the connecting member. The at least one driven shaft of the surgical instrument extends between and has a first end and a second end. The second end has an oblique end surface corresponding to the oblique end surface of the at least one drive shaft of the instrument drive unit.

The method further includes engaging the oblique end surface of the at least one drive shaft of the instrument drive unit with the oblique end surface of the at least one driven shaft of the surgical instrument via at least one of a first connection pathway and a second connection pathway. The second connection pathway is oriented transversely relative to the first connection pathway.

In aspects of the present disclosure, engaging the oblique end surfaces via the first connection pathway may include translating the instrument drive unit and the surgical instrument toward one another along a vertical axis intersecting the at least one drive shaft of the instrument drive unit and the at least one driven shaft of the surgical instrument. In some embodiments, engaging the oblique end surfaces via the second connection pathway may include translating the instrument drive unit and the surgical instrument toward one another along a horizontal axis. It is contemplated that the horizontal axis may be oriented perpendicularly to the vertical axis.

In some embodiments, the method may further include orienting the oblique end surface of the at least one drive shaft of the instrument drive unit to face a first direction. Translating the instrument drive unit and the surgical instrument toward one another may include translating the surgical instrument towards the instrument drive unit along the horizontal axis in a second direction. The second direction may be oriented opposite the first direction.

It is envisioned that the oblique end surfaces can be configured such that upon engagement of the second end of the at least one drive shaft of the instrument drive unit with the second end of the at least one driven shaft of the surgical instrument, the at least one driven shaft may rotate to orient the oblique end surface of the at least one driven shaft into flush engagement with the oblique end surface of the at least one drive shaft. Each oblique end surface defines a plane such that when corresponding oblique end surfaces are engaged, the planes of the corresponding oblique end surfaces may be parallel to one another.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the present disclosure are described herein with reference to the accompanying drawings, wherein.

DETAILED DESCRIPTION

Embodiments of the presently disclosed interface, systems and methods thereof are described in detail with reference to the drawings, in which like reference numerals designate identical or corresponding elements in each of the several views. As used herein the term "distal" refers to that portion of the surgical instrument and/or instrument drive unit that is closer to the patient, while the term "proximal" refers to that portion of the surgical instrument and/or instrument drive unit that is farther from the patient.

Figure 1:
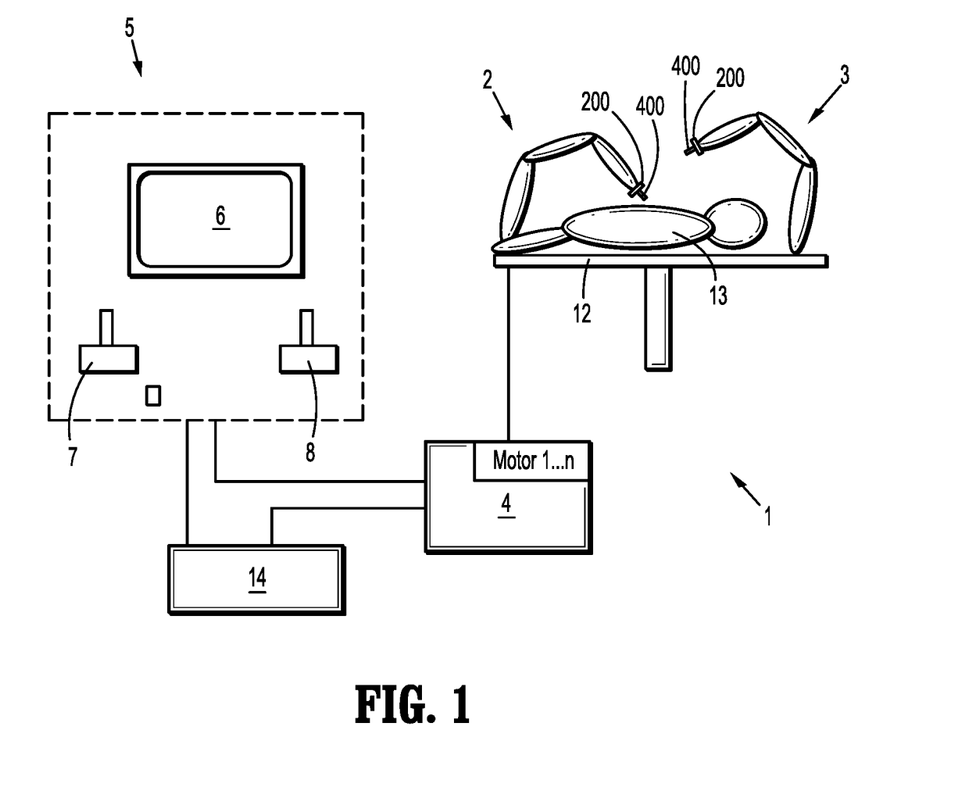
FIG. 1 is a schematic illustration of a surgical system in accordance with the present disclosure.

Referring initially to FIG. 1, a surgical system, such as, for example, a robotic surgical system is shown generally as surgical system 1 and generally includes a plurality of robotic arms 2, 3; a control device 4; and an operating console 5 coupled with control device 4. Operating console 5 includes a display device 6, which is set up in particular to display three-dimensional images; and manual input devices 7, 8, by means of which a person (not shown), for example a surgeon, is able to telemanipulate robotic arms 2, 3 in a first operating mode, as known in principle to a person skilled in the art.

Each of the robotic arms 2, 3 includes a plurality of members, which are connected through joints, and an instrument drive unit 200, to which may be attached, for example, a connection member 402 of a surgical instrument 400 supporting an end effector (not shown), in accordance with any one of several embodiments disclosed herein, as will be described in greater detail below.

Robotic arms 2, 3 may be driven by electric drives (not shown) that are connected to control device 4. Control device 4 (e.g., a computer) is set up to activate the drives, in particular by means of a computer program, in such a way that robotic arms 2, 3, their instrument drive units 200 and thus the surgical instrument 400 (including end effector) execute a desired movement according to a movement defined by means of manual input devices 7, 8. Control device 4 may also be set up in such a way that it regulates the movement of robotic arms 2, 3 and/or of the drives.

Surgical system 1 is configured for use on a patient 13 lying on a patient table 12 to be treated in a minimally invasive manner by means of an end effector. Surgical system 1 may also include more than two robotic arms 2, 3, the additional robotic arms likewise being connected to control device 4 and being telemanipulatable by means of operating console 5. A surgical instrument 400 (including an end effector) may also be attached to the additional robotic arm.

Reference may be made to U.S. Pat. No. 8,828,023, filed on Nov. 3, 2011, entitled "Medical Workstation," the entire content of which is incorporated herein by reference, for a detailed discussion of the construction and operation of surgical system 1.

Control device 4 may control a plurality of motors (Motor 1 . . . n) with each motor configured to wind-up or let out a length of a cable (not shown) extending through each robot arm to an end effector of surgical instrument 400. In use, as cables are wound-up and let out, cables effect operation and/or movement of each end effector of surgical instrument 400. It is contemplated that control device 4 coordinates the activation of the various motors (Motor 1 . . . n) to coordinate a winding-up or letting out a length of a respective cable in order to coordinate an operation and/or movement of a respective end effector. In embodiments, each motor can be configured to actuate a drive rod or a lever arm to effect operation and/or movement of each end effector of surgical instrument 400. In some instances, two or more cables or two ends of a single cable may be wound up or let out by a single motor. For example, in some instances, two cables or cable ends may be coupled in opposite directions to a single motor so that as the motor is activated in a first direction, one of the cables winds up while the other cable lets out. Other cable configurations may be used in different embodiments.

Turning to FIGS. 2-10, an interface 100 for surgical system 1 connects a connection hub 202 of an instrument drive unit 200 of robotic arms 2 and/or 3 with a connecting member 402 of a surgical instrument 400 having an end effector (not shown). Interface 100 is established between instrument drive unit 200 and surgical instrument 400. Instrument drive unit 200 is disposed with a distal end of robotic arms 2 and/or 3 and is configured to actuate movement of surgical instrument 400 and various articulations of the end effector (not shown).

Figure 2:
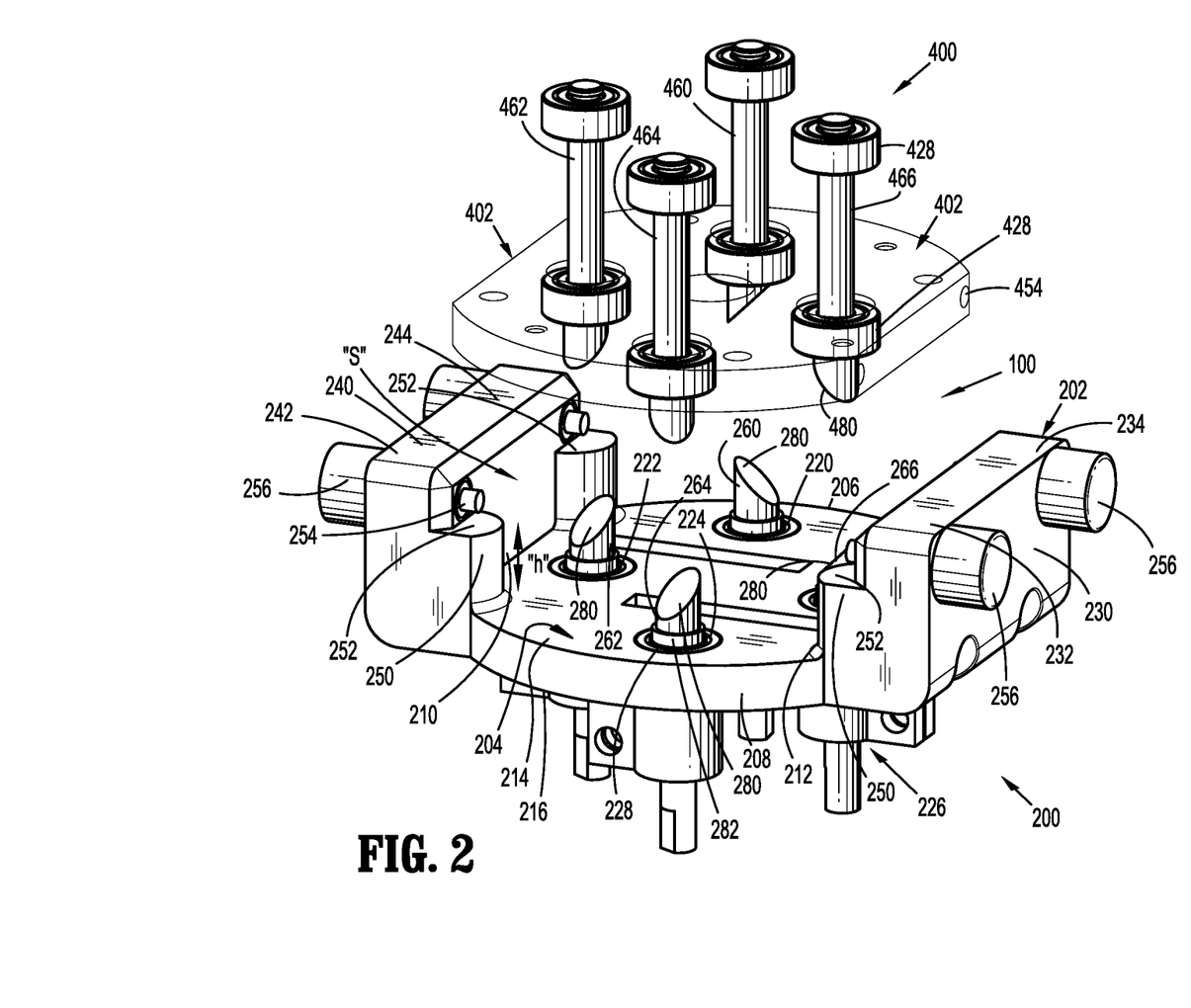
FIG. 2 is a perspective view, in part phantom, of one embodiment of an interface for a surgical system in accordance with the principles of the present disclosure.
Figure 3:
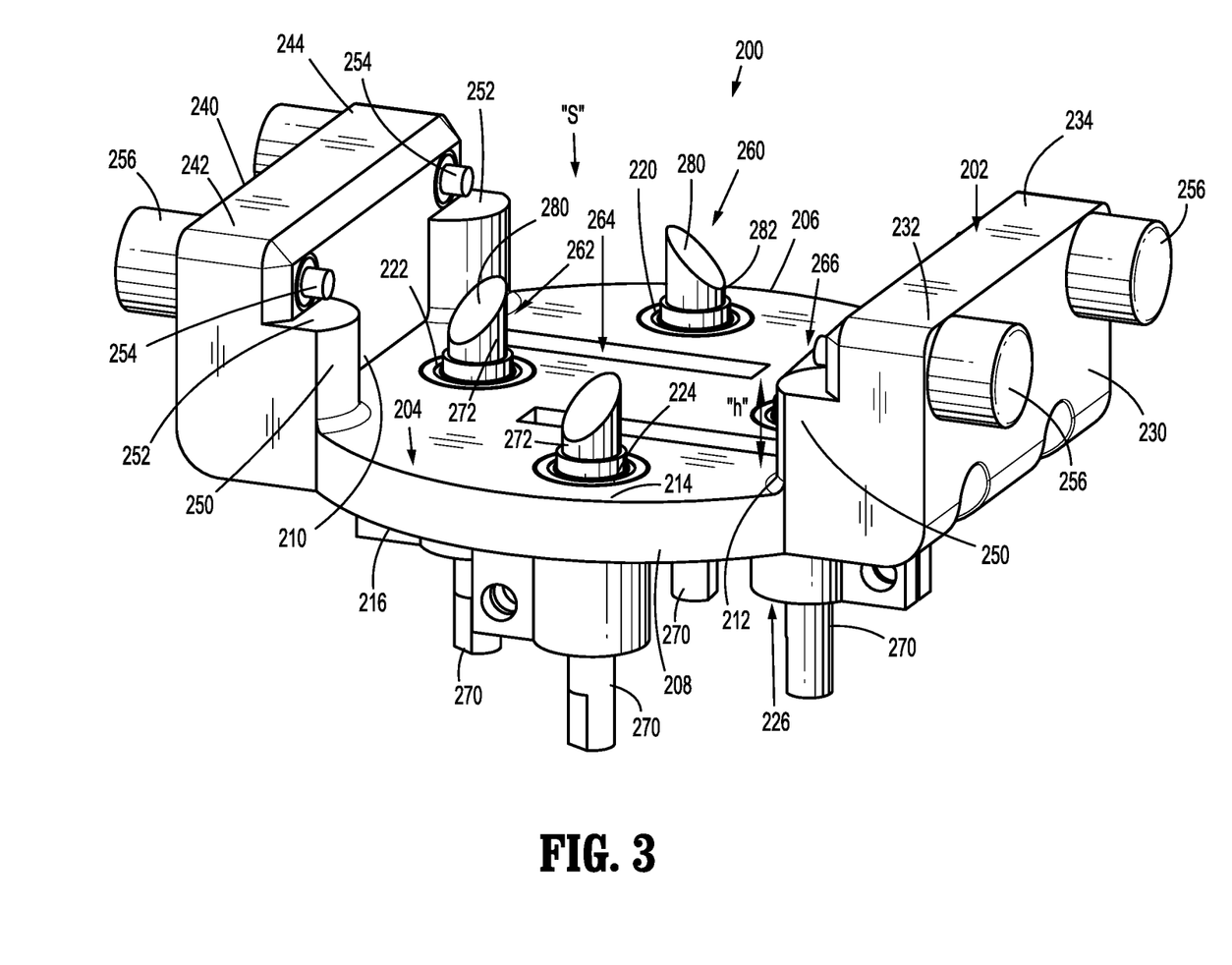
FIG. 3 is a perspective view of a connection hub of an instrument drive unit shown in FIG. 2.

Instrument drive unit 200 includes a connection hub 202 configured for receipt of connecting member 402 of surgical instrument 400 and selective securement therewith. Connection hub 202 includes a base portion 204 having a pair of opposing sides 206, 208 and a pair of opposing planar sides 210, 212. In some embodiments, base portion 204 is variously configured, such as for example, oval, oblong, triangular, arcuate, rectangular, square, tapered and/or polygonal. Base portion 204 includes a first planar surface 214 and a second planar surface 216. A plurality of bores 220, 222, 224, 226 extend through planar surfaces 214, 216 of base portion 204. Each bore 220, 222, 224, 226 is configured for disposal of a bearing, such as, for example, a ball bearing 228, which are each configured to rotatably support a respective drive shaft 260, 262, 264, 266, as described herein below. As shown in the illustrated embodiment, bores 220, 222, 224, 226 are spaced from one another in a staggered configuration. In some embodiments, bores 220, 222, 224, 226 are aligned in a symmetrical configuration or any other configuration.

Figure 7:
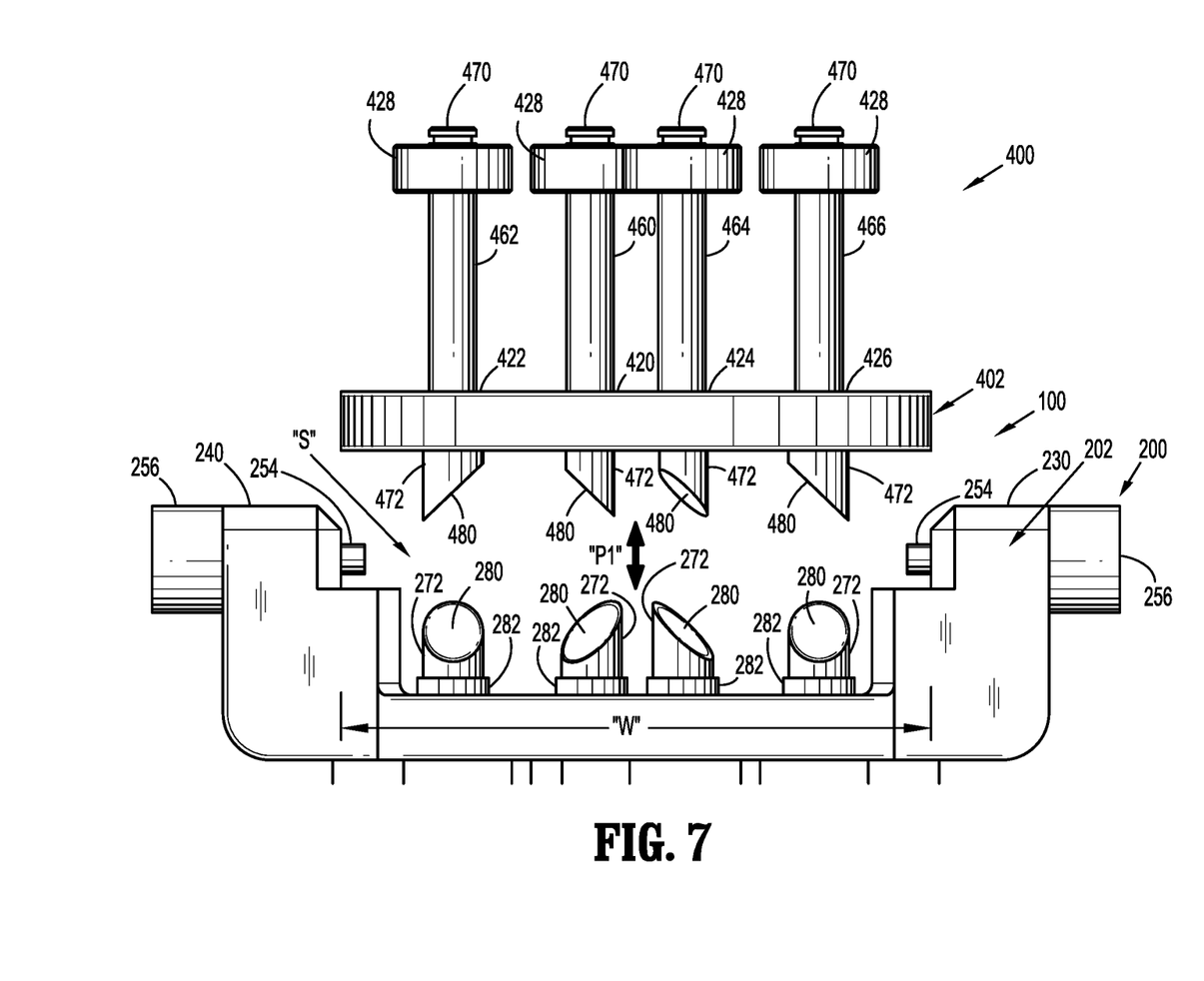
FIG. 7 is a side view of the connection hub and the connecting member of the interface shown in FIG. 2 being connected via a first connection pathway.

Connection hub 202 of instrument drive unit 200 includes a pair of spaced apart opposed sidewalls 230, 240 extending therefrom. Specifically, sidewalls 230, 240 are monolithically formed or integrally connected with planar sides 210, 212 of base portion 204 and extend perpendicularly therefrom. Desirably, sidewalls 230, 240 may be parallel with one another. Sidewall 230 extends between a first end 232 and a second end 234 and sidewall 240 extends between a first end 242 and a second end 244. Base portion 204 and sidewalls 230, 240 define a space or cavity "S" having a width "W" therebetween (FIG. 7). Width "W" of space or cavity "S" defined between sidewalls 230, 240 is substantially equal to a width of connecting member 402 of surgical instrument 400 such that connecting member 402 can be seated substantially flush between sidewalls 230, 240 of connection hub 202 of instrument drive unit 200, as described herein below.

With continued reference to FIG. 2, first and second ends 232, 234 of sidewall 230 and first and second ends 242, 244 of sidewall 240 each include a lateral step 250 defining a planar face or ledge 252. Planar faces or ledges 252 extend in a plane that is parallel to base portion 204 so that connecting member 402 of surgical instrument 400 is parallel to base portion 204 when seated on planar faces or ledges 252 of connection hub 202 of instrument drive unit 200. Further, connecting member 402 of surgical instrument 400 is elevated or spaced from first surface 214 of base portion 204 by a height "h" equal to a height of step 250, as shown in FIG. 2.

First and second ends 232, 234 of sidewall 230 and first and second ends 242, 244 of sidewall 240 each include an axially translatable protrusion 254 configured for receipt in a cavity 454 of connecting member 402 to detachably secure connection hub 202 and connecting member 402 to one another. Each protrusion 254 overlaps a respective one of planar faces or ledges 252. Protrusions 254 include a body portion 256 that can be pulled to axially translate protrusion 254 relative to a respective sidewall 230, 240 and out of cavity 454 of connecting member 402. Protrusions 254 include a biasing member (not shown) to resiliently bias protrusions 254 to protrude from a respective sidewall 230, 240 and into space or cavity "S" of connection hub 202.

In use, upon positioning connecting member 402 of surgical instrument 400 within space or cavity "S," connecting member 402 engages protrusions 254 to overcome the resilient bias of each protrusion 254. Protrusions 254 are caused to axially translate into their respective sidewalls 230, 240 and out of space S. Upon connecting member 402 being seated on planar faces 252 of steps 250, protrusions 254, due to their resilient bias, extend back out of sidewalls 230, 240 and into cavities 454 of connecting member 402 to secure connection hub 202 of instrument drive unit 200 with connecting member 402 of surgical instrument 400. It is contemplated that connection hub 202 can be secured with connecting member 402 via various connection mechanisms to resist and/or prevent relative movement in the vertical direction.

As mentioned above, instrument drive unit 200 includes a plurality of drive shafts, such as, for example, first, second, third and fourth drive shafts 260, 262, 264, 266. In some embodiments, instrument drive unit 200 includes more or less than four drive shafts. Drive shafts 260, 262, 264, 266 are rotatably supported in connection hub 202 within bores 220, 222, 224, 226, respectively. Drive shafts 260, 262, 264, 266 have a substantially cylindrical configuration and may be non-cannulated. In some embodiments, all or portions of drive shafts 260, 262, 264, 266 are alternatively configured, such as, for example, square, rectangular, oval, oblong, tapered, polygonal, non-circular, cannulated with thick walls, tubular and/or conical. Drive shafts 260, 262, 264, 266 are rotatably supported in connection hub 202 in a staggered configuration. In embodiments, drive shafts 260, 262, 264, 266 are spaced along a longitudinal axis such that drive shafts 260, 262, 264, 266 are rotatably supported in connection hub 202 in a straight-lined configuration.

Figure 5A:
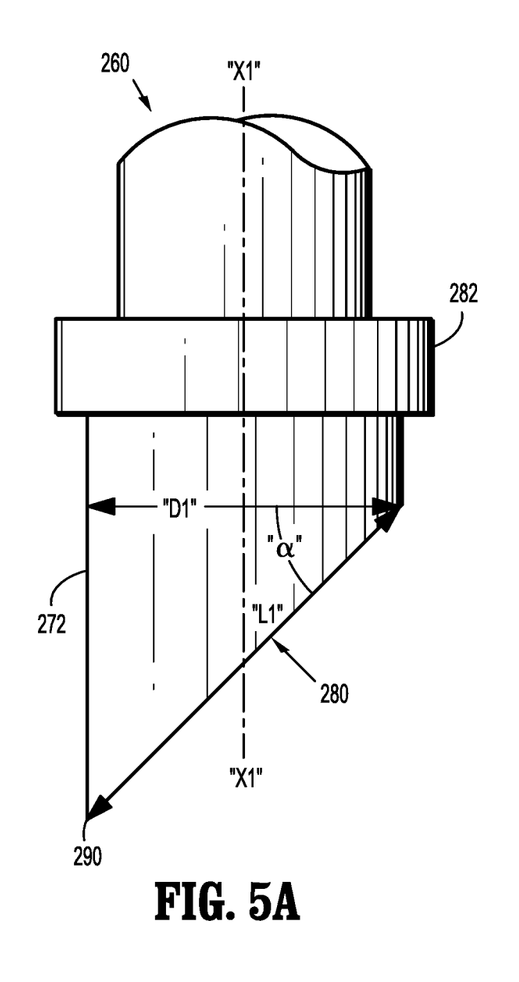
FIGS. 5A-5B are side views of an oblique end surface of a drive shaft of the connection hub of the instrument drive unit shown in FIG. 3 and an oblique end surface of a driven shaft of the connecting member of the surgical instrument shown in FIG. 4.

As shown at least in FIGS. 2, 3 and 5A, each drive shaft 260, 262, 264, 266 extends between a first end 270 and a second end 272, and defines a respective longitudinal axis "X1" therealong. First ends 270 are configured for connection with a motor (Motor 1 . . . n) that drives rotational movement of drive shafts 260, 262, 264, 266 within bores 220, 222, 224, 226. Second ends 272 extend substantially perpendicularly from first planar surface 214 of base portion 204 and into space or cavity "S."

Second ends 272 of each drive shaft 260, 262, 264, 266 include an oblique end surface 280 having an ovate configuration. In some embodiments, oblique end surfaces 280 are variously configured, such as, for example, oval, oblong, square, tapered, textured, roughened, knurled, convex, concave, tapered, polygonal and/or undulating. Oblique end surfaces 280 of drive shafts 260, 262, 264, 266 of instrument drive unit 200 are configured for engagement with corresponding oblique end surfaces 480 of driven shafts 460, 462, 464, 466 of surgical instrument 400 to transfer torque therebetween, as described herein below. Oblique end surfaces 280 define an angle "α" relative to a longitudinal axis "X1" of drive shafts 260, 262, 264, 266, as shown in FIG. 5A. In some instances angle "α" may be approximately 30 to 60 degrees. In an instance angle "α" may be approximately 45 degrees. Oblique end surfaces 280 have a length "L1" that is greater than a diameter "D1."

Each oblique end surface 280 may define a plane such that, when a corresponding oblique end surface of driven shafts 460, 462, 464, 466 of surgical instrument 400 engages a respective oblique end surface 280 of drive shafts 260, 262, 264, 266 of instrument drive unit 200, the planes of the corresponding oblique end surfaces 280, 480 are parallel to one another, as described herein below. In other instances, each oblique end surface 280 may define a contoured surface that has curves, peaks, valleys, and other non-flat regions. In such instances, the contoured end surfaces of shafts 460, 462, 464, 466 of surgical instrument 400 may be shaped to engage and mate with the corresponding contoured end surfaces of shafts 260, 262, 264, 266 of drive unit 200 during a coupling of the surgical instrument 400 to the drive unit 200 as described herein.

Second end 272 of each drive shaft 260, 262, 264, 266 of instrument drive unit 200 further includes a radial extension or flange 282 disposed adjacent oblique end surface 280 thereof. Flanges 282 are engaged with first planar surface 214 of base portion 204 to maintain oblique end surfaces 280 projecting from bores 220, 222, 224, 226 and within space or cavity As briefly described above, interface 100 is established between surgical instrument 400 and instrument drive unit 200, which are releasably connectable to one another. A distal end of surgical instrument 400 is configured for detachable engagement with an end effector (not shown). Surgical instrument 400 includes a connecting member 402, and respective first, second, third and fourth driven shafts 460, 462, 464, 466 rotatably supported in connecting member 402.

Figure 4:
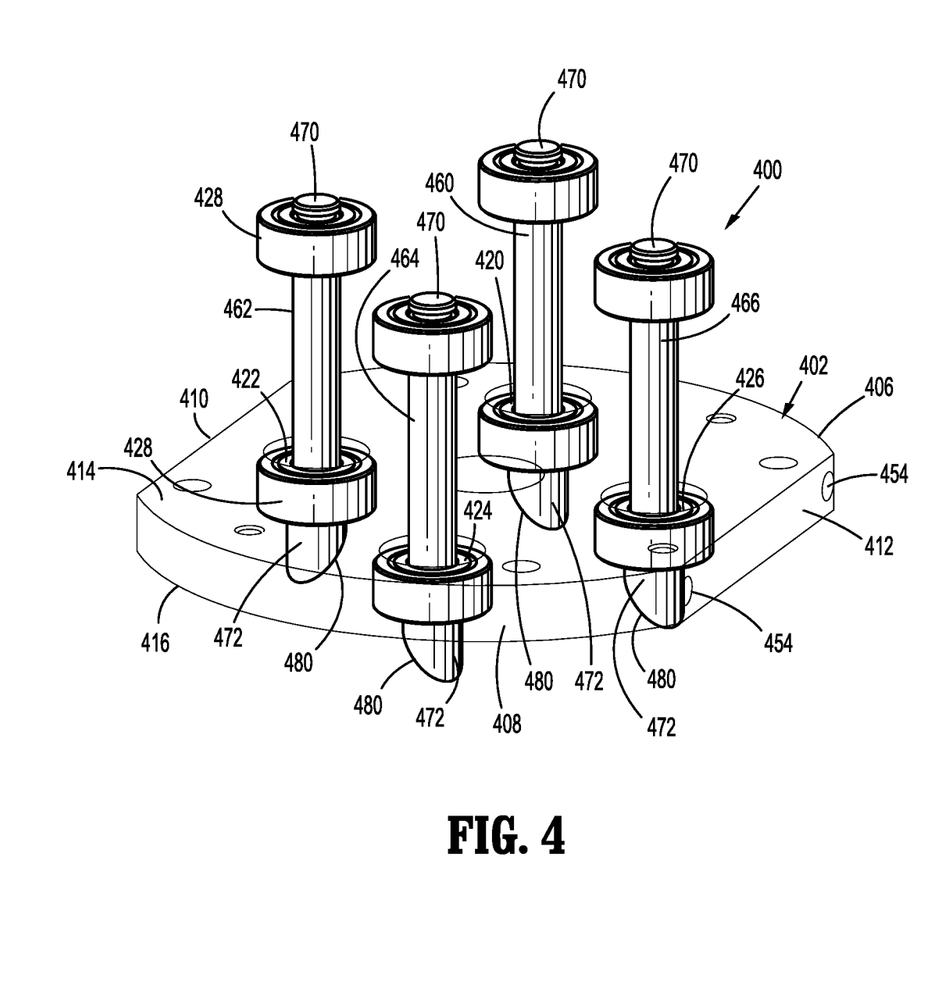
FIG. 4 is a perspective view of a connecting member of a surgical instrument shown in FIG. 2.

As shown in FIGS. 2 and 4, connecting member 402 is configured as a rectangular plate. However, it is contemplated that connecting member 402 is variously configured, such as for example, oval, oblong, triangular, square, tapered and/or polygonal. Connecting member 402 includes a pair of opposing sides 406, 408 corresponding to sides 206, 208 of base portion 204 of connection hub 202. Connecting member 402 also includes a pair of opposing planar sides 410, 412 corresponding to planar sides 210, 212 of base portion 204 of connection hub 202. Upon engagement of connecting member 402 of surgical instrument 400 with connection hub 202 of instrument drive unit 200, planar sides 410, 412 of connecting member 402 are in parallel alignment with sidewalls 230, 240 of connection hub 202. Sidewalls 230, 240 and planar faces 252 of steps 250 of connection hub 202 act as a guide for sliding and/or lowering connecting member 402 into space or cavity "S" and thereby into securement with connection hub 202.

Planar sides 410, 412 of connecting member 402 each include a pair of cavities 454 defined therein configured for receipt of axially translatable protrusions 254 of connection hub 202. Cavities 454 on planar side 410 are spaced from one another a distance that is equal to a distance that protrusions 254 of sidewall 240 are spaced from one another. Cavities 454 on planar side 412 are spaced a distance from one another that is equal to a distance that protrusions 254 of sidewall 230 are spaced from one another. In this way, protrusions 254 can be inserted within respective cavities 454 of connecting member 402 to detachably secure connection hub 202 and connecting member 402. It is contemplated that connection hub 202 can be secured with connecting member 402 via various connection mechanisms to resist and/or prevent relative movement in the vertical direction.

Connecting member 402 includes a first planar surface 414, and an opposed second planar surface 416. A plurality of bores 420, 422, 424, 426 extend through planar surfaces 414, 416 of connecting member 402. Each bore 420, 422, 424, 426 is configured for disposal of a bearing, such as, for example, a ball bearing 428, which are each configured to rotatably support a respective driven shaft 460, 462, 464, 466 of surgical instrument 400, as described herein below. In some embodiments, the bearing can be variously configured, such as, for example, as a bushing or a thrust bearing. In some embodiments, bores 420, 422, 424, 426 may not include a bearing. As shown in the illustrated embodiment, bores 420, 422, 424, 426 are spaced from one another in a staggered configuration, similar to bores 220, 222, 224, 226 of connection hub 202. When connecting member 402 is seated on steps 250 of connection hub 202 and protrusions 254 of connection hub 202 are aligned with respective cavities 454 of connecting member 402, bores 420, 422, 424, 426 of connecting member 402 are coaxial with bores 220, 222, 224, 226 of connection hub 202, respectively. In some embodiments, bores 420, 422, 424, 426 are aligned in a symmetrical configuration or any other configuration.

As mentioned above, surgical instrument 400 includes a plurality of driven shafts, such as, for example, first, second, third and fourth driven shafts 460, 462, 464, 466, respectively, similar to drive shafts 260, 262, 264, 266 described above with regard to instrument drive unit 200. In some embodiments, surgical instrument 400 includes more or less than four driven shafts. Driven shafts 460, 462, 464, 466 are rotatably supported in connecting member 402 within bores 420, 422, 424, 426, respectively. Driven shafts 460, 462, 464, 466 have a substantially cylindrical configuration and may be non-cannulated or cannulated having relatively thick walls. In some embodiments, driven shafts 460, 462, 464, 466 are alternatively configured, such as, for example, those alternatives described herein. Driven shafts 460, 462, 464, 466 are rotatably supported in connecting member 402 in a staggered configuration. In one embodiment, driven shafts 460, 462, 464, 466 may be rotatably supported in connecting member 402 in a straight-lined configuration.

Figure 5B:
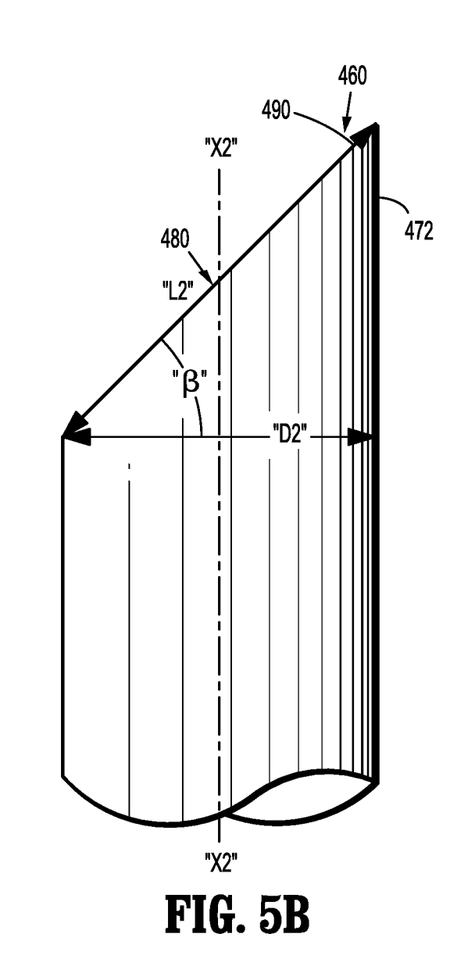

Driven shafts 460, 462, 464, 466 each extend between a first end 470 and a second end 472, and define a respective longitudinal axis "X2" therealong, as shown in FIG. 5B. First ends 470 are configured for connection with an end effector. First ends 470 of driven shafts 460, 462, 464, 466 have ball bearings 428 disposed thereabout. Second ends 472 extend substantially perpendicularly from second planar surface 416 of connecting member 402. As mentioned above, the bearing can be variously configured, such as, for example, as a bushing or a thrust bearing. It is also contemplated that bores 420, 422, 424, 426 may not include a bearing.

Figure 6:
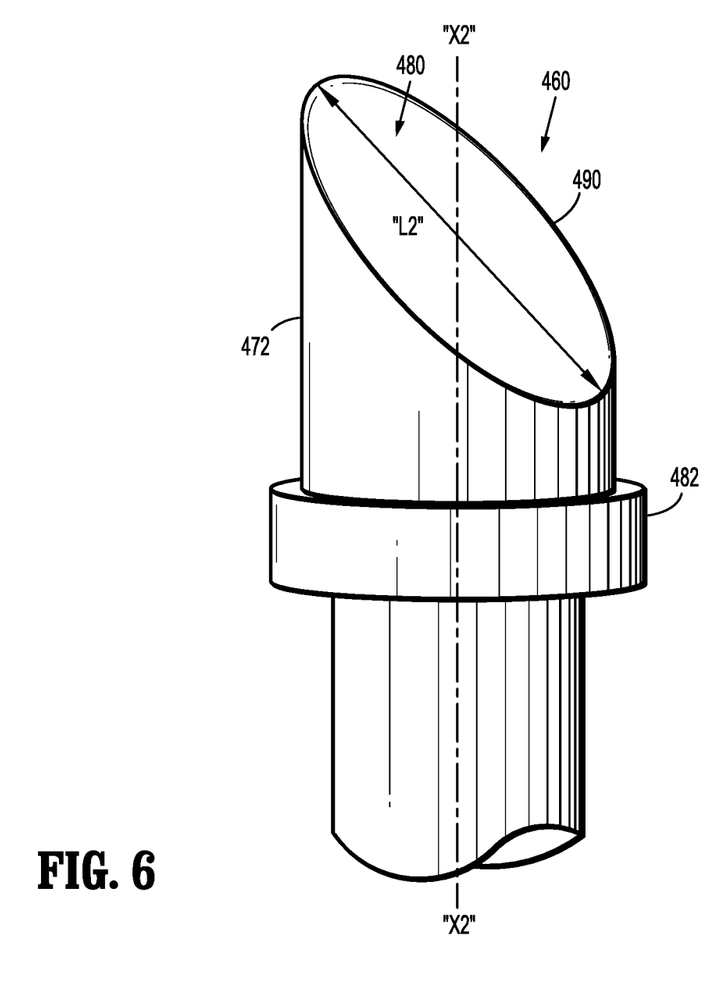
FIG. 6 is a perspective view of the oblique end surface of the driven shaft of the connecting member of the surgical instrument shown in FIG. 5B.

Second ends 472 of each driven shaft 460, 462, 464, 466 include an oblique end surface 480, similar to or complimentary to oblique end surfaces 280 of drive shafts 260, 262, 264, 266 of instrument drive unit 200, described herein above. Oblique end surfaces 480 of driven shafts 460, 462, 464, 466 of connecting member 402 are configured for engagement with oblique end surfaces 280 of drive shafts 260, 262, 264, 266 of instrument drive unit 200 to receive torque therefrom. In some embodiments, drive shafts 260, 262, 264, 266 and/or driven shafts 460, 462, 464, 466 include interlocking features to further restrict and/or prevent relative rotation therebetween thereby enhancing the transfer of torque and inhibiting slippage from occurring therebetween. It is contemplated that various interlocking features can be included, such as, for example, a latch lock, mating parts, snap fit, interference fit, friction fit and/or texturing, roughening or knurling of oblique end surfaces 280, 480.

Oblique end surfaces 480 define an angle "β" relative to longitudinal axis "X2" of driven shafts 460, 462, 464, 466 that may be equal to angle "α" of oblique end surfaces 280 of drive shafts 260, 262, 264, 266 of instrument drive unit 200. Oblique end surfaces 480 have a length "L2" that is greater than a diameter "D2" of driven shafts 460, 462, 464, 466. Angle "α" of oblique end surfaces 280 of drive shafts 260, 262, 264, 266 and angle "β" of oblique end surfaces 480 of driven shafts 460, 462, 464, 466 provide for a resistance and/or prevention of relative rotation between drive shafts 260, 262, 264, 266 of instrument drive unit 200 and driven shafts 460, 462, 464, 466 of surgical attachment 400 when oblique end surfaces 280 and oblique end surfaces 480 are engaged (i.e., abutting engagement).

Each oblique end surface 480 defines a plane such that, when a corresponding oblique end surface 280 of drive shafts 260, 262, 264, 266 is engaged thereto, the planes of the corresponding oblique end surfaces 280, 480 are parallel to one another. Upon engagement of oblique end surfaces 280 of drive shafts 260, 262, 264, 266 with oblique end surfaces 480 of corresponding driven shafts 460, 462, 464, 466, drive shafts 260, 262, 264, 266 are in coaxial alignment with driven shafts 460, 462, 464, 466 and instrument drive unit 200 and surgical attachment 400 are constrained from moving relative to one another in the vertical direction.

In one embodiment, oblique end surfaces 280 of drive shafts 260, 262, 264, 266 may be concave and oblique end surfaces 280 of driven shafts 460, 462, 464, 466 may be convex, or vice versa. In some embodiments, oblique end surfaces 280, 480 are variously configured, such as, for example, oval, oblong, planar, undulating, square, rectangular, triangular, polygonal and/or tapered.

In embodiments, perimeter edges 290, 490 of each oblique end surface 280, 480 are rounded, beveled or squared.

Figure 10:
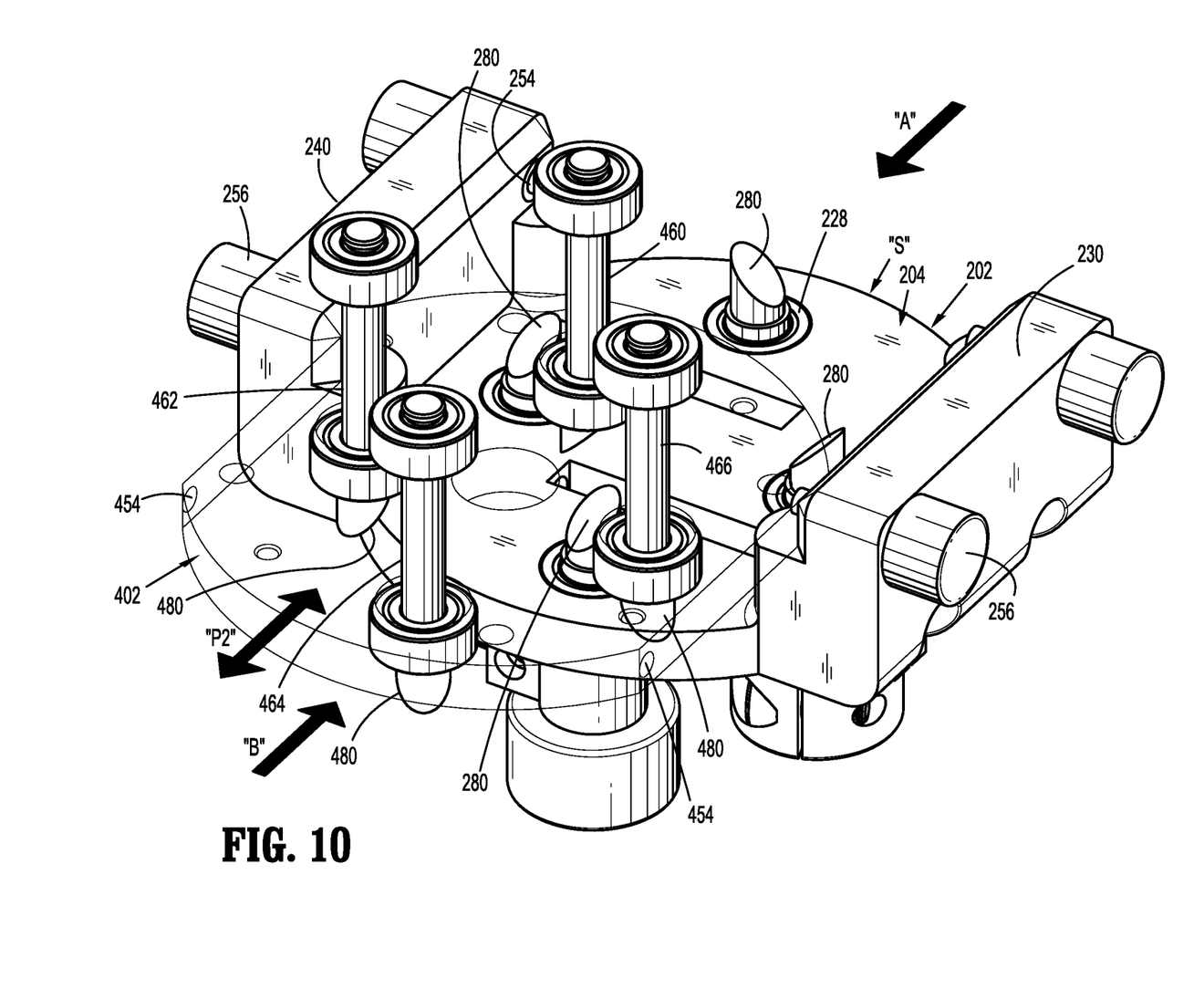
FIG. 10 is a perspective view, in part phantom, of the connection hub and connecting member of the interface shown in FIG. 2 being connected along a second connection pathway.

Oblique end surfaces 280, 480 are configured such that connecting member 402 of surgical instrument 400 is connectable with connection hub 202 of instrument drive unit 200 via a first connection pathway "P1," as shown in FIG. 7, and a second connection pathway "P2," as shown in FIG. 10. First connection pathway "P1" is oriented transversely relative to second connection pathway "P2." In the illustrated embodiment, first connection pathway "P1" is oriented substantially perpendicularly to second connection pathway "P2." First connection pathway "P1" extends in an axis parallel with longitudinal axis "X1" of drive shafts 260, 262, 264, 266 and longitudinal axis "X2" of driven shafts 460, 462, 464, 466. Second connection pathway "P2" extends in an axis that runs parallel with and between longitudinal axes defined by sidewalls 230, 240 of connection hub 202, or an axis that runs perpendicular to longitudinal axes "X1" and "X2" of drive shafts 260, 262, 264, 266 and driven shafts 460, 462, 464, 466, respectively.

In operation, surgical instrument 400 and instrument drive unit 200 are connected with one another, as described above, via either first connection pathway "P1" or second connection pathway "P2." To engage surgical instrument 400 to instrument drive unit 200 via first connection pathway "P1," surgical instrument 400 and instrument drive unit 200 are translated toward one another along first connection pathway "P1," as shown in FIG. 7. For example, connecting member 402 of surgical instrument 400 can be translated along first connection pathway "P1" toward connection hub 202 of instrument drive unit 200 to engage second ends 472 of driven shafts 460, 462, 464, 466 of surgical instrument 400 with second ends 272 of drive shafts 260, 262, 264, 266 of instrument drive unit 200. Oblique end surfaces 280, 480 are configured such that oblique end surfaces 480 of driven shafts 460, 462, 464, 466 can be connected to oblique end surfaces 280 of drive shafts 260, 262, 264, 266 of instrument drive unit 200 despite their relative orientations about longitudinal axis "X2" and "X1," respectively.

Figure 8A:
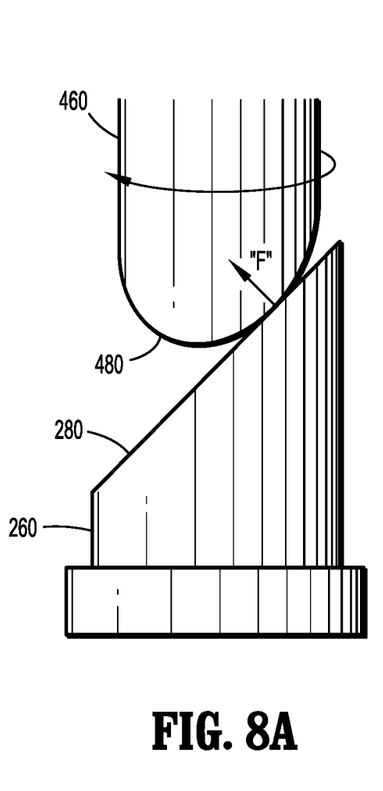
FIGS. 8A-8C are side, expanded views of the oblique end surfaces of the interface shown in FIG. 2 upon engagement of said oblique end surfaces with one another.

The angled configuration of oblique end surfaces 280, 480 and the continued application of a force on surgical instrument 400 along first connection pathway "P1" causes the driven shafts 460, 462, 464, 466 to rotate relative to drive shafts 260, 262, 264, 266 of instrument drive unit 200, as shown in FIG. 8A. A reactive force "F," oriented perpendicular to oblique end surfaces 280, exerted by oblique end surfaces 280 on oblique end surfaces 480, drives the rotation of oblique end surfaces 480 relative thereto.

Figure 8B:
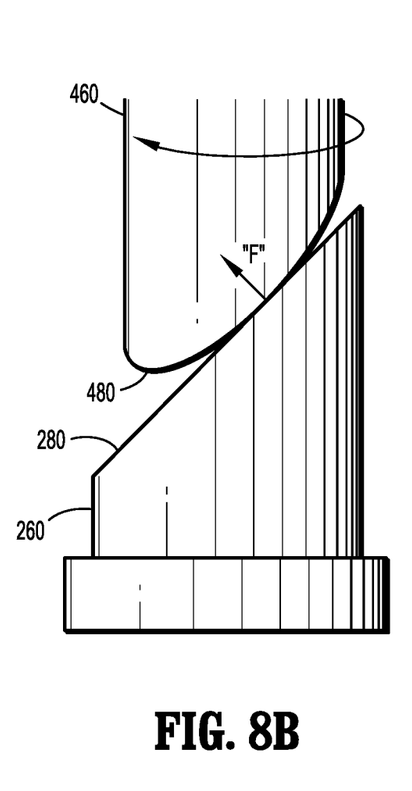
Figure 8C:
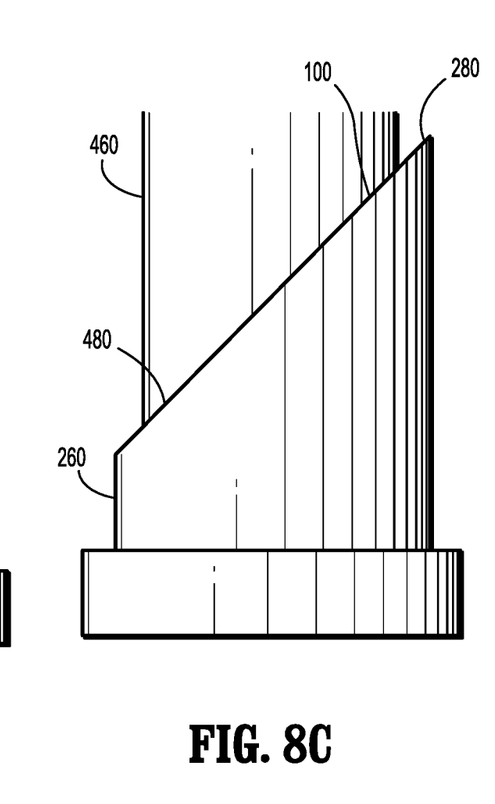
Figure 9:
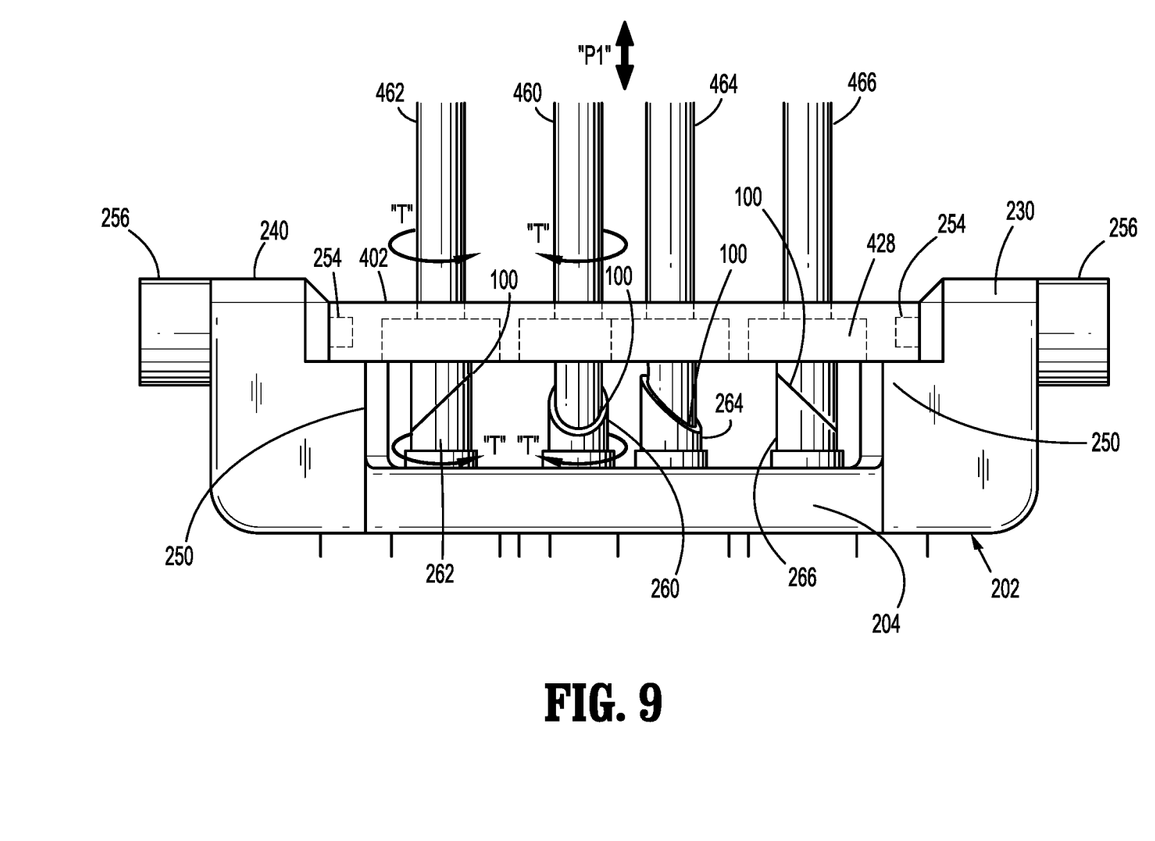
FIG. 9 is a side view, in part phantom, of the connection hub and connecting member of the interface shown in FIG. 2 in connection with one another.

Driven shafts 460, 462, 464, 466 of surgical instrument 400 continue to rotate, as shown in FIG. 8B, until oblique end surfaces 480 of driven shafts 260, 262, 264, 266 are oriented into flush engagement or abutment with oblique end surfaces 280 of drive shafts 260, 262, 264, 266 of instrument drive unit 200, as shown in FIG. 8C. Upon the flush engagement or abutment of oblique end surfaces 480 of surgical instrument 400 and oblique end surfaces 280 of instrument drive unit 200, as shown in FIGS. 8C and 9, relative rotation between drive shafts 260, 262, 264, 266 and driven shafts 460, 462, 464, 466 is resisted and/or prevented. In this way, rotation of drive shafts 260, 262, 264, 266 of instrument drive unit 200 can transmit a torque "T" to driven shafts 460, 462, 464, 466 of surgical instrument 400 to actuate functions of an end effector (not shown) of surgical instrument 400.

To connect surgical instrument 400 to instrument drive unit 200 via the second connection pathway "P2," drive shafts 260, 262, 264, 266 may be disposed with instrument drive unit 200 in a staggered configuration so that drive shafts 260, 262, 264, 266 do not block one another. Oblique end surfaces 280 of drive shafts 260, 262, 264, 266 of instrument drive unit 200 are oriented to face a first direction, indicated by arrow "A" in FIG. 10. Connecting member 402 of surgical instrument 400 is translated along second connection pathway "P2" in a second direction, indicated by arrow "B" in FIG. 10, toward connection hub 202 of instrument drive unit 200 to engage or abut second ends 472 of driven shafts 460, 462, 464, 466 of surgical instrument 400 with second ends 270 of drive shafts 260, 262, 264, 266 of instrument drive unit 200.

The angled configuration of oblique end surfaces 280, 480 and the continued application of a force on surgical instrument 400 along second connection pathway "P2," in the direction indicated by arrow "B," causes driven shafts 460, 462, 464, 466 to rotate relative to drive shafts 260, 262, 264, 266 of instrument drive unit 200. Driven shafts 460, 462, 464, 466 of surgical instrument 400 continue to rotate until oblique end surfaces 480 of driven shafts 460, 462, 464, 466 are oriented into flush engagement or abutment with oblique end surfaces 280 of drive shafts 260, 262, 264, 266 of instrument drive unit 200. Upon the flush engagement or abutment of oblique end surfaces 480 of surgical instrument 400 and oblique end surfaces 280 of instrument drive unit 200, relative rotation between drive shafts 260, 262, 264, 266 and driven shafts 460, 462, 464, 466 is resisted and/or prevented. In this way, rotation of drive shafts 260, 262, 264, 266 of instrument drive unit 200 can transmit torque "T" to driven shafts 460, 462, 464, 466 of surgical instrument 400 to actuate functions of an end effector (not shown) of surgical instrument 400.

Oblique end surfaces 480 of driven shafts 460, 462, 464, 466 can be connected to oblique end surfaces 280 of drive shafts 260, 262, 264, 266 of instrument drive unit 200 despite the orientations of oblique end surfaces 480 about longitudinal axes "X1" and "X2" relative to oblique end surfaces 280.

Upon the flush connection of oblique end surfaces 480 of surgical instrument 400 with oblique end surfaces 280 of instrument drive unit 200 (via either first or second connection pathways "P1," "P2"), connecting member 402 is received in space or cavity "S" of connection hub 202 and seated on planar faces or ledges 252 of steps 250. Protrusions 254 of connection hub 202 engage cavities 454 of connecting member 402 to secure connecting member 402 with connection hub 202 so that vertical movement (i.e., movement along first connection pathway "P1") and/or horizontal movement (i.e., movement along second connection pathway "P2") of connecting member 402 relative to connection hub 202 is resisted and/or prevented. Further, securing connecting member 402 with connection hub 202 resists and/or prevents oblique end surfaces 480 from sliding relative to oblique end surfaces 280.

Figure 11:
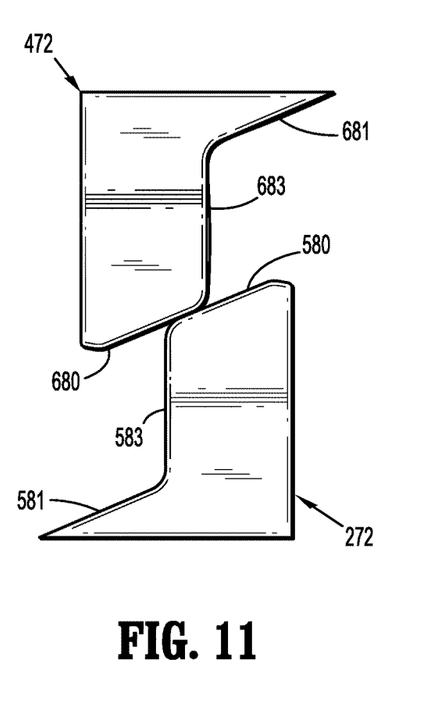
FIGS. 11-13 are progressive side views of an alternate embodiment of an interface according to the present disclosure illustrating end surfaces thereof being connected along a vertical connection pathway.
Figure 12:
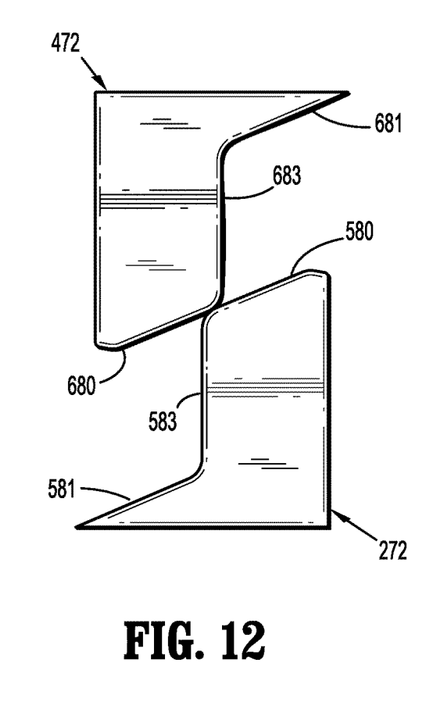
Figure 13:
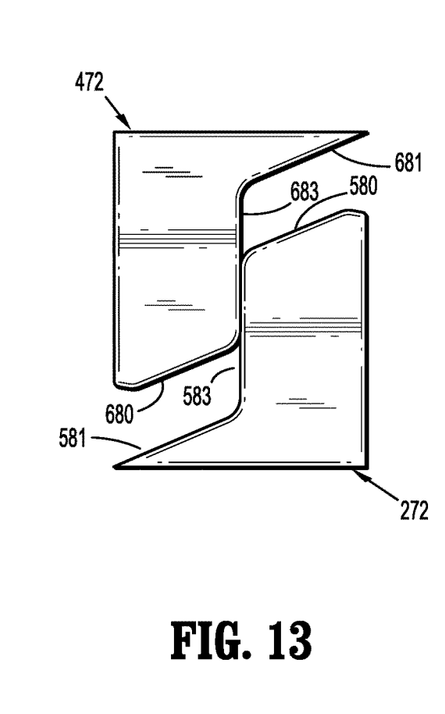

In one embodiment, as shown in FIGS. 11-13, second ends 272, 472 of drive shafts 260, 262, 264, 266 and driven shafts 460, 462, 464, 466, respectively, are alternatively configured. Second ends 272, 472 each include a first oblique end surface 580, 680, respectively, similar to oblique end surfaces 280, 480 described above, and a second oblique end surface 581, 681. First oblique end surfaces 580, 680 are axially spaced relative to corresponding second oblique end surfaces 581, 681 and are interconnected by a vertically-oriented surface 583, 683. Oblique end surfaces 580, 581 extend from surface 583 at an obtuse angle, and oblique end surfaces 680, 681 extend from surface 683 at an obtuse angle. It is contemplated that surfaces 583, 683 may have a planar configuration.

It will be understood that various modifications may be made to the embodiments disclosed herein. For example, while the cam pulleys disclosed herein have been shown and described as being connected to the proximal ends of the jaws, it is contemplated and within the scope of the present disclosure, for the cam pulley to be operatively connected with the distal portion of the jaws. Therefore, the above description should not be construed as limiting, but merely as exemplifications of various embodiments. Those skilled in the art will envision other modifications within the scope and spirit of the claims appended thereto.

What is claimed is:

1. A method of assembling a surgical system, comprising:
   providing an instrument drive unit including:
      a connection hub; and
      at least one drive shaft rotatably supported in the connection hub, the at least one drive shaft extending between and having a first end configured for connection with a motor and a second end, the second end having an oblique end surface;
   providing a surgical instrument including:
      a connecting member; and
      at least one driven shaft rotatably supported in the connecting member, the at least one driven shaft of the surgical instrument extending between and having a first end and a second end, the second end having an oblique end surface corresponding to the oblique end surface of the at least one drive shaft of the instrument drive unit; and
   engaging the oblique end surface of the at least one drive shaft of the instrument drive unit with the oblique end surface of the at least one driven shaft of the surgical instrument.

2. The method according to claim 1, wherein the oblique end surface of the at least one drive shaft of the instrument drive unit is engaged with the oblique end surface of the at least one driven shaft of the surgical instrument via a first connection pathway or a second connection pathway.

3. The method according to claim 2, wherein the second connection pathway is oriented transversely relative to the first connection pathway.

4. The method according to claim 2, wherein engaging the oblique end surfaces via the first connection pathway includes translating the instrument drive unit and the surgical instrument toward one another along a vertical axis intersecting the at least one drive shaft of the instrument drive unit and the at least one driven shaft of the surgical instrument, and wherein engaging the oblique end surfaces via the second connection pathway includes translating the instrument drive unit and the surgical instrument toward one another along a horizontal axis, the horizontal axis oriented perpendicularly to the vertical axis.

5. The method according to claim 4, further comprising orienting the oblique end surface of the at least one drive shaft of the instrument drive unit to face a first direction, wherein translating the instrument drive unit and the surgical instrument toward one another includes translating the surgical instrument towards the instrument drive unit along the horizontal axis in a second direction, the second direction oriented opposite the first direction.

6. The method according to claim 1, wherein the oblique end surfaces are configured such that upon engagement of the second end of the at least one drive shaft of the instrument drive unit with the second end of the at least one driven shaft of the surgical instrument, the at least one driven shaft rotates to orient the oblique end surface of the at least one driven shaft into flush engagement with the oblique end surface of the at least one drive shaft.

7. The method according to claim 1, wherein each oblique end surface defines a plane such that when corresponding oblique end surfaces are engaged, the planes of the corresponding oblique end surfaces are parallel to one another and relative rotation therebetween is resisted.

8. A method of assembling a surgical system, comprising engaging an oblique end surface of a driven shaft of a surgical instrument with an oblique end surface of a drive shaft of an instrument drive unit, thereby operably coupling the surgical instrument to the instrument drive unit.

9. The method according to claim 8, further comprising rotating at least one of the driven shaft of the surgical instrument or the drive shaft of the instrument drive unit in response to the oblique end surfaces engaging one another.

10. The method according to claim 9, wherein at least one of the driven shaft of the surgical instrument or the drive shaft of the instrument drive unit rotates until the oblique end surfaces are in flush engagement with one another.

11. The method according to claim 8, wherein the oblique end surface of the drive shaft of the instrument drive unit is engaged with the oblique end surface of the driven shaft of the surgical instrument via a first connection pathway or a second connection pathway.

12. The method according to claim 11, wherein the second connection pathway is oriented transversely relative to the first connection pathway.

13. The method according to claim 12, wherein the oblique end surfaces are engaged via the first connection pathway, which includes translating the instrument drive unit and the surgical instrument toward one another along a vertical axis intersecting the drive shaft of the instrument drive unit and the driven shaft of the surgical instrument.

14. The method according to claim 12, wherein the oblique end surfaces are engaged via the second connection pathway, which includes translating the instrument drive unit and the surgical instrument toward one another along a horizontal axis, the horizontal axis oriented perpendicularly to the vertical axis.

15. A method of connecting a surgical instrument to a robotic arm, comprising:
aligning a plurality of driven shafts of a surgical instrument with a plurality of drive shafts of an instrument drive unit;
engaging an end portion of each of the plurality of driven shafts with an end portion of each of the plurality of drive shafts; and
rotating at least one of:
the plurality of driven shafts about their respective longitudinal axes; or
the plurality of drive shafts about their respective longitudinal axes, such that the end portions of the plurality of driven shafts matingly engage the end portions of the corresponding plurality of drive shafts.

16. The method according to claim 15, wherein the end portion of at least one of the plurality of driven shafts includes an oblique end surface, and the end portion of at least one of the plurality of drive shafts includes an oblique end surface, the oblique end surfaces abutting one another upon the end portions of the plurality of driven shafts matingly engaging the end portions of the corresponding plurality of drive shafts.

17. The method according to claim 16, wherein each oblique end surface defines a plane such that when the oblique end surfaces are engaged, the planes of the oblique end surfaces are parallel to one another and relative rotation therebetween is resisted.

18. The method according to claim 15, wherein the engagement of the end portion of each of the plurality of driven shafts with the end portion of each of the plurality of drive shafts causes at least one of:
the plurality of driven shafts to rotate about their respective longitudinal axes; or
the plurality of drive shafts to rotate about their respective longitudinal axes.

19. The method according to claim 15, wherein the end portion of each of the plurality of drive shafts is engaged with the end portion of each of the plurality of driven shafts via a first connection pathway or a second connection pathway.

20. The method according to claim 19, wherein the second connection pathway is oriented transversely relative to the first connection pathway.

* * * * *